United States Patent
Elhawary et al.

(10) Patent No.: US 10,194,801 B2
(45) Date of Patent: Feb. 5, 2019

(54) FIBER OPTIC SENSOR GUIDED NAVIGATION FOR VASCULAR VISUALIZATION AND MONITORING

(71) Applicant: KONINKLIJKE PHILIPS N.V., Eindhoven (NL)

(72) Inventors: Haytham Elhawary, New York, NY (US); Aleksandra Popovic, New York, NY (US); Robert Manzke, Bonebuttel (DE); Raymond Chan, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 976 days.

(21) Appl. No.: 14/407,970

(22) PCT Filed: Jun. 20, 2013

(86) PCT No.: PCT/IB2013/055064
§ 371 (c)(1),
(2) Date: Dec. 15, 2014

(87) PCT Pub. No.: WO2014/001977
PCT Pub. Date: Jan. 3, 2014

(65) Prior Publication Data
US 2015/0141808 A1 May 21, 2015

Related U.S. Application Data

(60) Provisional application No. 61/665,387, filed on Jun. 28, 2012.

(51) Int. Cl.
*A61B 5/05* (2006.01)
*A61B 5/00* (2006.01)
(Continued)

(52) U.S. Cl.
CPC ........ *A61B 5/0026* (2013.01); *A61B 1/00009* (2013.01); *A61B 5/0084* (2013.01);
(Continued)

(58) Field of Classification Search
CPC .......... A61B 17/00008; A61B 17/0057; A61B 17/068; A61B 19/5244; A61B 1/00009;
(Continued)

(56) References Cited

U.S. PATENT DOCUMENTS 6,453,906 B1  9/2002  Taylor et al.
8,150,535 B2  4/2012  Tockman et al.
(Continued)

FOREIGN PATENT DOCUMENTS

JP   2009095447 A   5/2009
JP   2011189074 A   9/2011
(Continued)

OTHER PUBLICATIONS

Figl, Michael et al "Augmented Reality Image Guidance for Minimally Invasive Coronary Artery Bypass" Proc. SPIE 6918, Medical Imaging 2008: Visualization, Image-guided Procedures, and Modeling.

*Primary Examiner* — Amelie R Gillman

(57) ABSTRACT

A method for visualizing branches of a lumen includes inserting (402) a fiber optic shape sensing device into a lumen and determining (404) changes in the lumen based upon strain induced in the fiber optic shape sensing device by flow in the lumen. Locations of branches are indicated (410) on a rendering of the lumen. An instrument is guided (414) to the locations of branches indicated on the rendering.

16 Claims, 4 Drawing Sheets

(51) Int. Cl.
| | |
|---|---|
| *A61B 5/06* | (2006.01) |
| *A61B 1/00* | (2006.01) |
| *A61B 5/02* | (2006.01) |
| *A61B 5/026* | (2006.01) |
| *A61B 5/107* | (2006.01) |
| *A61B 17/068* | (2006.01) |
| *A61B 34/20* | (2016.01) |
| *A61B 34/30* | (2016.01) |
| *A61B 17/00* | (2006.01) |
| *A61B 90/00* | (2016.01) |

(52) U.S. Cl.
CPC ........ *A61B 5/02007* (2013.01); *A61B 5/0261* (2013.01); *A61B 5/065* (2013.01); *A61B 5/1076* (2013.01); *A61B 5/1079* (2013.01); *A61B 5/489* (2013.01); *A61B 5/4836* (2013.01); *A61B 5/6847* (2013.01); *A61B 5/7264* (2013.01); *A61B 17/00008* (2013.01); *A61B 17/0057* (2013.01); *A61B 17/068* (2013.01); *A61B 34/20* (2016.02); *A61B 34/30* (2016.02); *A61B 5/066* (2013.01); *A61B 5/6876* (2013.01); *A61B 2017/00778* (2013.01); *A61B 2034/2061* (2016.02); *A61B 2034/303* (2016.02); *A61B 2090/365* (2016.02)

(58) Field of Classification Search
CPC .. A61B 2017/00778; A61B 2034/2061; A61B 2034/303; A61B 2090/365; A61B 34/20; A61B 34/30; A61B 5/0084; A61B 5/02007; A61B 5/0261; A61B 5/065; A61B 5/066; A61B 5/1076; A61B 5/1079; A61B 5/4836; A61B 5/489; A61B 5/6847; A61B 5/6876; A61B 5/7264; A61B 5/026
See application file for complete search history.

(56) References Cited

U.S. PATENT DOCUMENTS

| | | | |
|---|---|---|---|
| 2002/0041723 A1* | 4/2002 | Ronnekleiv | A61B 5/0084 385/12 |
| 2002/0049375 A1* | 4/2002 | Strommer | A61B 5/0066 600/407 |
| 2004/0097805 A1 | 5/2004 | Verard | |
| 2004/0176688 A1* | 9/2004 | Haldeman | A61B 8/06 600/443 |
| 2005/0159764 A1* | 7/2005 | Kasahara | A61B 17/00008 606/159 |
| 2007/0156019 A1 | 7/2007 | Larkin et al. | |
| 2008/0154141 A1* | 6/2008 | Shuros | A61B 5/0031 600/505 |
| 2010/0030063 A1* | 2/2010 | Lee | A61B 5/06 600/424 |
| 2012/0050513 A1 | 3/2012 | Averbuch et al. | |
| 2012/0071894 A1 | 3/2012 | Tanner | |
| 2012/0215094 A1* | 8/2012 | Rahimian | A61B 1/00193 600/414 |
| 2013/0041360 A1* | 2/2013 | Farritor | A61B 18/1445 606/29 |
| 2013/0190726 A1* | 7/2013 | Kesner | A61M 25/0105 604/510 |

FOREIGN PATENT DOCUMENTS

| | | |
|---|---|---|
| WO | 2010111090 A1 | 9/2010 |
| WO | 2011083374 A1 | 7/2011 |
| WO | 2011101754 A1 | 8/2011 |
| WO | 2012035492 A1 | 3/2012 |
| WO | 2012042413 A1 | 4/2012 |
| WO | 2013030764 A1 | 3/2013 |
| WO | 2013093761 A1 | 6/2013 |

* cited by examiner

FIBER OPTIC SENSOR GUIDED NAVIGATION FOR VASCULAR VISUALIZATION AND MONITORING

CROSS-REFERENCE TO PRIOR APPLICATIONS

This application is the U.S. National Phase application under 35 U.S.C. § 371 of International Application No. PCT/IB2013/055064, filed on Jun. 20, 2013, which claims the benefit of U.S. Provisional Patent Application No. 61/665,387, filed on Jun. 28, 2012. These applications are hereby incorporated by reference herein.

This disclosure relates to medical instruments and more particularly to shape sensing optical fibers in medical applications for identifying and accessing branches of a lumen.

Coronary artery bypass grafting (CABG) is a surgical procedure for revascularization of obstructed coronary arteries. In conventional surgery, a patient's sternum is opened and the heart is fully exposed. An important part of this procedure is the removal of a vessel from the patient's body, which is then used to bypass one or more atherosclerotic narrowings in the coronary arteries. A vessel most commonly used is the Internal Mammary Artery (IMA) which is located in the chest. Other vessels used include the saphenous vein (leg) and the radial artery (arm).

Minimally invasive (MI) bypass surgery is performed through small ports (e.g., having an opening size of about 5 mm for totally endoscopic procedures and between about 50-60 mm for MI direct bypass surgery). During MI cardiac bypass surgery, direct access to the vessels used for replacement in the bypass is not available, and the vessels are removed using long instruments inserted into ports. During MI surgery, a surgical assistant can hold an endoscope, or the endoscope can be held using robotic guidance. In the case of robotic guidance, visual servoing can be used to move the robot to a specific location. Visual servoing includes selecting a point on the endoscope image, with the robot moving to maintain the point in the center of the image.

The vessels which are used in cardiac revascularization are often embedded in fat and fascia, and for their removal they need to be carefully excised from the surrounding tissue. In addition, the vessels present many small branches, which have to be cut and sealed using staples or cauterization to avoid leakage through the vessels once the bypass has been performed. This is a very demanding part of the procedure and is often the most time consuming, especially during MI surgery. Vision during this part is provided exclusively through an endoscope inserted through a thoracic port. Under these constraints, the branches can often be missed, leading them to be inadvertently cut without being stapled or cauterized in an adequate manner. This can lead to leakage of blood through these side branches, often requiring a repeat revascularization and further surgery.

In accordance with the present principles, a method for visualizing, accessing and/or monitoring branches of a lumen includes inserting a fiber optic shape sensing device into a lumen and determining branches in the lumen based upon strain induced by changes in flow in the lumen in the fiber optic shape sensing device. Locations of branches are indicated on a rendering of the lumen. An instrument is guided to the locations of branches indicated on the rendering.

In another embodiment, a method for visualizing, accessing and/or monitoring flow in a branched lumen includes inserting a fiber optic shape sensing device into a lumen; determining a position of the lumen and locations of branches from the lumen based upon changes to flow in the lumen resulting from strain induced fluctuations measured by the fiber optic shape sensing device; imaging a portion of the lumen to provide a real-time image; registering the real-time image with the position of the lumen measured by the fiber optic shape sensing device; and generating an overlay image indicating the position of the lumen and the locations of branches on the real-time image.

A system for monitoring a blood vessel includes a processor, a memory coupled to the processor, and a sensing and interpretation module stored in the memory and configured to interpret fiber optic shape sensing data from a fiber optic shape sensing device inserted in a blood vessel wherein the shape sensing data determines branches of the blood vessel. An image generation module is stored in the memory and configured to generate an overlay image based on the fiber optic shape sensing data indicating a shape of the blood vessel and locations of the branches from the blood vessel. A display is configured to render the overlay image over a rendering of the blood vessel to provide a guide for finding and operating on the branches of the blood vessel.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 1:
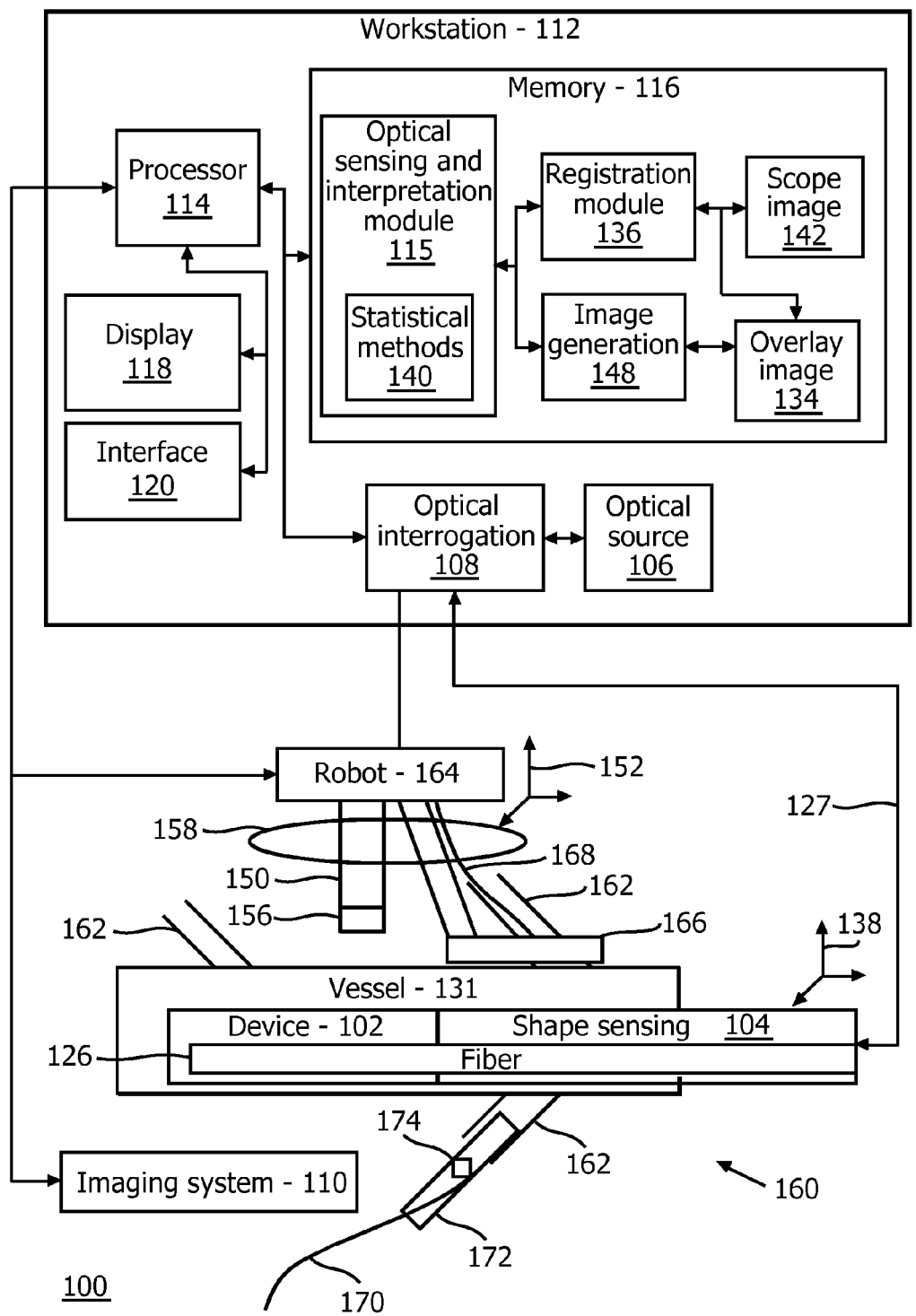
FIG. 1 is a block/flow diagram showing a shape sensing system which is employed for generating an overlay for guiding a surgical tool or device in accordance with one embodiment.

In accordance with the present principles, systems and methods are provided that employ Fiber Optic Shape Sensing and Localization (FOSSL) technology to improve and simplify coronary artery bypass grafting (CABG) or other surgical procedures. FOSSL technology or optical fiber shape sensing makes optical fibers sensitive to strain and temperature. Surrogate variables such as flow, inflammation, tissue pressure/swelling, tissue contact, etc., can be measured indirectly (using, in the case of flow, for example, temperature gradients of indicator dilution). The fibers, when embedded in a vessel, can provide the 3D shape and dynamics of the vasculature, as well as flow information to help detect branches and bifurcations.

In one embodiment, a procedure is performed using an intraluminally disposed shape sensing fiber optic device inserted into a vessel to be taken down, e.g., a Left Internal Mammary Artery (LIMA). A three-dimensional (3D) reconstruction of shape and flow information of the vessel (as obtained from shape sensing fiber(s)) is obtained, which permits computations for locating of side branches. Registration between a shape sensing coordinate frame and a robotic endoscope coordinate frame can be made to overlay the vessel to be taken down and its branches with shape sensor based 3D reconstruction data on the endoscope image. Visual servoing of the robotic endoscope based on selected points either on the endoscope image, or points of the 3D shape sensor based reconstruction can be performed.

It should be understood that the present invention will be described in terms of medical instruments for performing bypass surgery or other grafting procedures; however, the teachings of the present invention are much broader and are applicable to any internal procedure. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk read only memory (CD-ROM), compact disk read/write (CD-R/W), Blu-Ray™ and DVD.

Referring now to the drawings in which like numerals represent the same or similar elements and initially to FIG. 1, a system 100 for monitoring a lumen, such as a blood vessel, using shape sensing enabled devices is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an optical sensing and interpretation module 115 configured to interpret optical feedback signals from a shape sensing device or system 104. Optical sensing module 115 is configured to use the optical signal feedback (and any other feedback, e.g., electromagnetic (EM) tracking) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc.

Optical sensing module 115 may include models and/or statistical methods 140 for evaluating the shape sensing data to provide geometric relationships and states of the shape sensing device or system 104. The statistically methods 140 may include known algorithms adapted to evaluate the shape sensing data to determine flow and other characteristics of the structures being evaluated. The shape sensing system 104 on device 102 includes one or more optical fibers 126 which are coupled to the device 102 in a set pattern or patterns. The optical fibers 126 connect to the workstation 112 through cabling 127. The cabling 127 may include fiber optics, electrical connections, other instrumentation, etc., as needed.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

The device 102 may be inserted into a lumen, e.g., blood vessel 131. For example, the blood vessel 131 may include a blood vessel to be harvested, such as, an internal mammary artery (IMA), a saphenous vein, a radial artery or any other suitable blood vessel. A port and/or an incision may be employed to access the interior of the lumen and insert the device 102 including shape sensing device 104 with sensing fiber(s) 126. The shape sensing device 104 collects position data of the blood vessel 131. This includes the monitoring of motion due to blood flow and temperature fluctuations due to blood flow. The changes or fluctuations caused by blood flow can be monitored and/or accumulated over time to provide a map of branches 162. Statistical methods or models 140 in the optical sensing module 115 may indirectly compute the locations of branches 162 on the blood vessel 131.

In one embodiment, an endoscope or a robotically driven endoscope 150 includes a camera 156 mounted thereon for transmitting internal images to a display 118. The endoscope 150 and/or the camera 156 may be inserted through a port 158 or incision provided on a patient 160. The endoscope 150 or the camera 156 includes a coordinate system 152. The shape sensing device 104 also has its own coordinate system 138. These coordinate systems 138 and 152 can be registered so that data feedback from the shape sensing device can be employed to navigate the endoscope or robotically driven endoscope 150.

In one example, a registration method performed by or in conjunction with a registration module 136 may be employed to register the information from the sensing fiber 126 of device 104 onto endoscope images 142. In this case, the fiber coordinate frame 138 is registered to the coordinate frame 152 of the endoscope camera 156, after the camera 156 has been calibrated. One way to do this would be to point the endoscope 150 at a 3D phantom and then use a 3D reconstruction method (there are many known in art) to reconstruct the surface of the phantom. The sensing fiber 126 could then be used to "brush" over the same phantom surface reconstructing its own 3D shape. Both shapes could then be registered by registration module 136 using a method such as, e.g., an Iterative Closest Point (ICP) method, which is employed to minimize the difference between two clouds of points. ICP is often used to reconstruct 2D or 3D surfaces from different scans, to co-register anatomic models, etc. ICP would render the transformation matrix between the two coordinate frames. Other registration methods are also contemplated.

During a procedure, the device 102, equipped with the shape sensing device 104, is inserted into the blood vessel 131 and accumulates position data where the sensing device 104 has been within the vessel 131. Dynamic changes are recorded. Dynamic changes may be indirectly measured using temperatures differences, blood vessel motion, blood vessel stiffness, etc. In accordance with the present principles, the shape sensing data obtained by shape sensing device 104 will make it easier for a surgeon to visualize otherwise hidden branches extending from the vessel 131, as will be described.

Workstation 112 includes the display 118 for viewing internal images of the patient 160 with sensing data overlays of the blood vessel 131. An overlay image 134 may be generated by an image generation module 148 that takes the output (based on the shape sensing data) from the optical sensing module 115 and conveys the data dynamically in real-time in the overlay image 134. The overlay image 134 is registered with an endoscopic image 142 taken by camera 156 using the registration module 136. The overlay image 134 may include signposts or other indicators to indicate to the surgeon or robot where the branches 162 exist for the blood vessel 131. As the surgeon cuts and cauterizes or staples the branches 162, the overlay image 134 is updated based upon the blood flow data collected by the shape sensing device 104. In this way, the surgeon can easily see whether there are remaining branches 162 to be dealt with or even whether any previously cut branches 162 are still bleeding and need further attention.

Once the overlay has been performed, the surgeon can select the branch location and a robot 164 can move the endoscope 150 so that the branch location is centered in the displayed image (e.g., visual servoing). In one embodiment, the robot 164 can move the endoscope 150 along the blood vessel 131 and attend to each branch 162 and ensure that the sealing of each branch 162 is complete. In another embodiment, the endoscope 150 may move along one side of the artery first and then the other side. In another embodiment, a number of branches sensed by optical shape sensing device 104 can be displayed on display 118 in the endoscope image 142 (for example, a number (or count) of sealed off branches may be displayed in the image). As the flow measurement is continuous, the number can be updated as the surgeon seals the side branches.

Additionally, the physician can select a branch location on a 3D pre-operative image (e.g., a CT scan), and the robot 164 can move the endoscope 150 so that the branch is in the center of the endoscope image 142. In this case, the physician would select a location on the 3D representation or overlay image 134 of the vessel 131 from the fiber sensor (which would include a branch location from flow measurements), and the endoscope 150 would move so that the branch is in the center of the image. In this manner, even if the branch is not directly visible, the surgeon knows that it is located underneath the fat and fascia and can find it with tools.

In another embodiment, a desired graft vessel length and shape can be obtained from pre-operative images, such as X-ray coronary angiograms or CT scans using, e.g., imaging system 110. The preoperative images may be collected in advance by employing imaging system 110 of system 100 or by collecting the preoperative images at a different location or using a different system. During harvesting, a fiber sensor measurement using shape sensing device 104 can be used to find take-down vessel segments which are ideal given a predetermined vessel-graft wish list. A diameter can be interrogated with the device 104, which is included in a guidewire or other device (102). This acquires point clouds while the device 102 with the shape sensing device 104 is being maneuvered in the vessel 131. The spatial extent of points in the cloud would provide an estimate for the take-down vessel diameter.

In yet another embodiment, the shape sensing enabled device 102, e.g., a guidewire, may emit detectable (either visible or near infrared (IR) radiation), which can be detected with the endoscope camera (e.g., CCD camera) 156, e.g., as may be performed for ex-vivo tracking in optical coherence tomography (OCT) pull-back applied to harvested arterial specimens. OCT is an optical signal acquisition and processing method that captures micrometer-resolution, three-dimensional images from within optical scattering media (e.g., biological tissue). In this way, an end position of the device 102 can be visible through the harvest vessel tissue, indicating location during maneuvering and final positioning of the device 102. This can be used as an additional way of registering different coordinate spaces, harvesting constraints or to indicate 'no-go' areas, to prevent damage to the harvested tissue.

The system 100 may include or be employed with other devices and tools as well. For example, a cauterization tool 166 may include an integrated shape sensing fiber(s) 168. The tool 166 may include an intravascular flexible elongated radio frequency (RF) or laser cauterization device which can act either at a single location or in a spatially distributed fashion along the vessel length. Based on flow/shape measurements from the integrated fiber 168, the cauterization manifold (deployable balloon, filter, mesh, or tines) can be (semi-) automatically conformed to the shape of a lumen of the vessel 131 for targeted delivery of RF or photocoagulation therapy confined to the side branches 162, while simultaneously keeping the main vessel lumen patent.

In another embodiment, a shape sensing fiber(s) 170 may be integrated with a miniature intravascular imaging probe 172 that provides additional feedback about vessel anatomy and physiology. This probe 172 may include photoacoustic sensors 174 that are exquisitely sensitive to blood contrast, ultrasound sensors, infrared sensors for tissue spectroscopy and discrimination of fat and blood from other tissues, etc. The shape and flow sensing fiber feedback can be used to actuate the motion of a robotically-controlled endoluminal device (not shown) for side-branch cauterization.

Display 118 may permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

Figure 2:
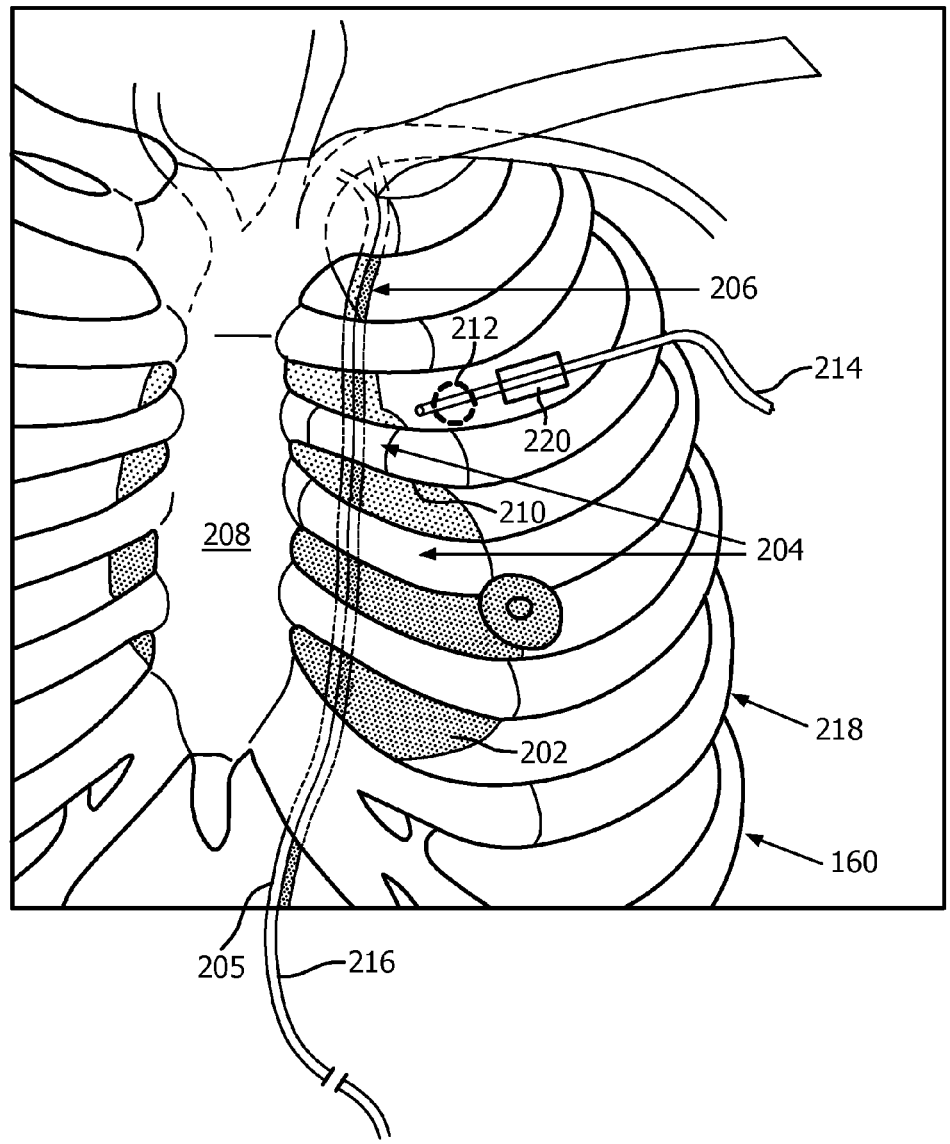
FIG. 2 is a diagram showing a shape sensing system inserted into a blood vessel of a patient and an endoscope inserted through a port into the patient in accordance with one illustrative embodiment.

Referring to FIG. 2, a diagram showing a rib cage 218 of a patient 160 illustrates an exemplary set up in accordance with one embodiment. The patient is depicted without flesh so that internal features can be seen. Below a sternum 208 is a heart 202. A left internal mammary artery (LIMA) 206 and vein 205 are shown running under ribs 204 with numerous branches 210, which in many instances run below the ribs 204. The LIMA 206 needs to be removed from the chest wall to be used in cardiac bypass.

A fiber optic shape sensing device 216 is inserted in the LIMA 206 to aid in the vessel take down during minimally invasive cardiac bypass surgery. The shape sensing device 216 is introduced into the vessel 206 that will be removed and used for bypass grafting. It should be understood that the present principles may also be applied to other commonly used vessels in cardiac bypass or other bypass surgery. In the case of LIMA 206, the device 216 can be introduced using a hybrid surgical endoluminal approach. The device 216 may include a catheter that can be introduced through a port or ports in a minimally invasive (MI) surgery and a small incision in the artery can be used to push the device 216 into the artery 206.

Once the device 216 is in place, the device 216 will provide information on the 3D shape of the vessel 206 as well as flow information at each point of an optical fiber(s) in the device 216. The presence of branches 210 will remove part of the flow from the main vessel 206, and can thus be detected with accuracy using optical fiber sensors of the device 216. Specifically, the optical fibers are capable of distributed volumetric flow sensing along their length.

In a single vessel without branch points, the volume flow rate along the length is continuous and uniform along the vessel centerline under steady state conditions. In the presence of a side-branch, the volume flow rate will drop along the length of the fiber sensor. Statistical methods for change detection can be applied to the distributed volume flow measurement along the sensor length to identify segments upstream and downstream of each side-branch location. In this manner, a 3D reconstruction of the vessel together with the location of the branches will be obtained as described above.

For example, an endoscope 214 may be inserted into a port 212 to provide images of the vessel 206. The shape sensing data may be overlaid in a display image to depict branches 210 to enable the surgeon to find and evaluate each branch 210. As this information is dynamic, it is also possible to assess the quality of cauterization of arteries as the LIMA takedown takes place. Thus, the surgeon can know if the branch 210 has been completely sealed in real-time.

The flow and 3D shape information of the vessel 206 is overlaid onto the endoscope images by a registration procedure. In this way, as the surgeon proceeds to take down the vessel from the chest wall using long instruments inserted into ports (e.g., 212), the shape of the vessel and the location of the branches 210 are viewed on the endoscope image to aid the vessel take down and to ensure all branches 210 are cut and sealed appropriately.

There are several registration methods to overlay the vessels on the endoscope image which can be used. For example, a method for augmented reality in an uncalibrated endoscope video may be employed by overlaying structures and 3D models from other imaging modalities. This would employ constructing a 3D image of the LIMA vessel from the shape sensing information, and indicating the location of branches at the positions of reduction of flow. This reconstructed 3D vessel would then be overlaid onto the endoscope image.

As the endoscope 214 may be mechanically coupled with a robotic system 220 (representatively shown in FIG. 2), a relative position of the endoscope image in the robotic coordinate frame can be derived through endoscope calibration procedures, known in art. As an alternative to calibration, which may introduce workflow issues during the surgery, the robotic system 220 can be steered using an un-calibrated method.

Figure 3B:
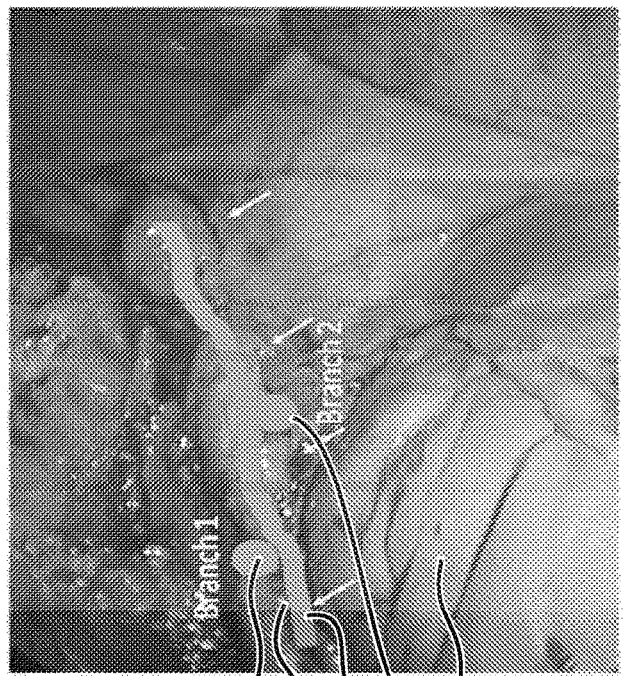
FIG. 3B is an image showing the internal mammary artery (IMA) of FIG. 3A having an overlay image registered thereto in accordance with one illustrative embodiment.
Figure 3A:
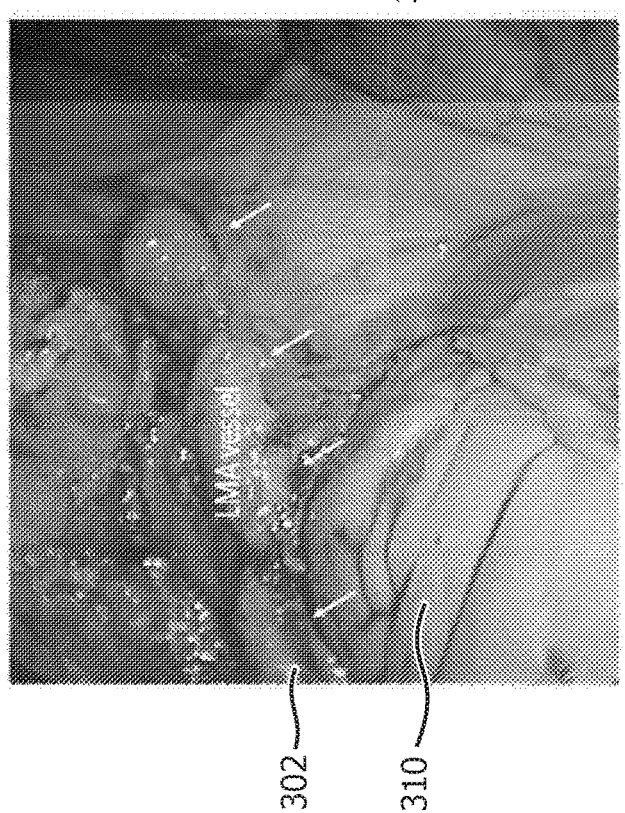
FIG. 3A is an image showing an internal mammary artery (IMA) taken down through a port using an endoscope.

Referring to FIG. 3A, an endoscope view of LIMA 302 is shown as indicated with white arrows. Some of its branches are hidden underneath fascia 310. During cardiac bypass surgery, a vessel, such as the LIMA 302 is removed from the patient's body and used to bypass an atherosclerotic narrowing in the coronary arteries. An important step of this procedure is the take down of the vessel to be used in the bypass grafting, which is often located in the chest, leg or arm. The vessel needs to be well preserved during take down to ensure adequate blood flow after bypass. In minimally invasive cardiac bypass, direct access to these vessels is not available, and they are removed using long instruments inserted into ports. These vessels need to have the numerous branches cut and stapled to stop potential leakage when bypass occurs. As these vessels are often embedded in fat and fascia 310, branches can often be missed, and so they are inadvertently cut without being stapled or blocked.

Referring to FIG. 3B, another endoscope view of LIMA 302 is shown as indicated with white arrows. An overlay image 306 of the LIMA 302 includes signposts 304 and 308 to indicate branches. Using robot guidance or manual guidance, the overlay image 306 with signposts 304 and 308 is employed to visualize or target the branches that would otherwise be buried or blocked from view by tissue. The overlay image 306 is generated using shape sensing feedback from a shape sensing device inserted within the LIMA 302.

While embodiments described herein are intended for minimally invasive coronary artery bypass grafting, other applications and situations are contemplated where endoscopic surgery is performed on blood vessels or employed for the removal of a vessel from a patient's body. In addition, the present principles may be employed in other surgical procedures in other parts of the body or in mechanical systems, including but not limited to training models, engines, plumbing systems, etc.

Figure 4:
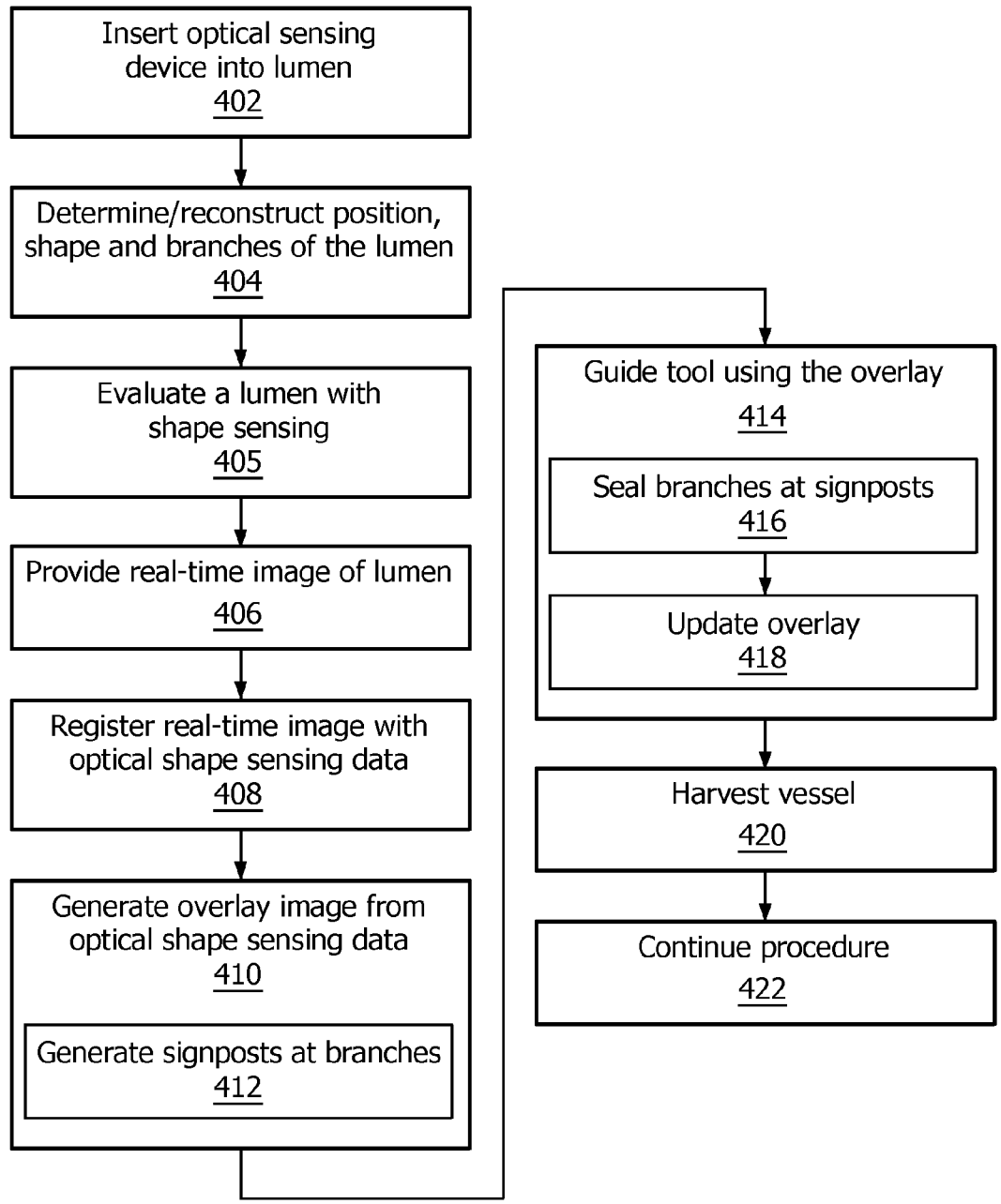
FIG. 4 is a flow diagram showing a method for accessing lumen branches using optical shape-sensing data in accordance with an illustrative embodiment.

Referring to FIG. 4, a method for visualizing a branched lumen is shown in accordance with illustrative embodiments. While the branched lumen may include a blood vessel, it should be understood that the branched lumen may include other structures as well. For example, the branched lumen may include other living tissues (e.g., bronchial tubes) or mechanical structures (e.g., plumbing, etc.). The illustrative embodiments described with respect to FIG. 4 will refer to surgical procedures and in particular takedown of a blood vessel. In block 402, after appropriate preparation, a fiber optic shape sensing device is inserted into a lumen of a blood vessel or the like. The fiber optic shape sensing device is positioned into a blood vessel to be harvested.

In block 404, a position of the lumen and locations of branches from the lumen are determined based upon changes to flow in the lumen. These changes are result from strain induced fluctuations measured by the fiber optic shape sensing device. In one embodiment, the geometry and/or shape of the lumen is reconstructed as a three-dimensional structure including branches. A statistical method may be employed for detecting changes in flow along a length of the lumen to detect the branches.

In one embodiment, the blood vessel may be evaluated using a fiber optic shape sensing device to determine a portion of the blood vessel suitable for a revascularization procedure in block 405. Other criteria for blood vessel or other lumen selection may also be employed.

In block 406, at least a portion of the lumen is imaged to provide a real-time image. The imaging may be provided using a scope (e.g., an endoscope) with a camera or other imaging device. The scope may be inserted into a patient to collect the image through a port. The scope may be robotically controlled. In block 208, the real-time image is registered with the position of the lumen measured by the fiber optic shape sensing device (shape sensing data). In block 410, an overlay image indicating the position of the lumen and the locations of branches is generated on the real-time image. This may be rendered on a display. In one embodiment, the lumen includes a branched blood vessel to be harvested for a bypass procedure. The lumen may include branches that are invisible due to surrounding tissues. The overlay image provides signposts on the overlay at locations of the branches to render the branches visible in block 412.

In block 414, a tool may be robot-guided to at least one of the locations of the branches as indicated in the overlay. Once guided to a branch location a plurality of different procedures or operations may be carried out. The robot guidance may employ a visual servoing method to center the endoscopic image on the overlay image. The robot or human guidance may also employ other techniques for tracking the lumen. In one example, in block 416, the branches in the lumen as indicated by the overlay are sealed off. This may include cauterizing, stapling, etc. the branches of the blood vessel. Since the overlay image is driven by the shape sensing data, which includes branch location information, the overlay may be updated using the shape sensing data to indicate whether the branches have been sealed off in block 418. In block 420, the blood vessel is harvested and prepared for revascularization in a bypass or other surgical procedure. In block 422, the procedure is continued, e.g., to complete the takedown or other tasks.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for fiber optic sensor guided navigation for vascular visualization and monitoring (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for monitoring a blood vessel, comprising:
   a processor;
   a memory coupled to the processor;
   a fiber optic shape sensing device configured to be inserted in a blood vessel for providing shape sensing data indicating blood flow in the blood vessel; and
   a display,
   wherein the memory includes instructions, when executed by the processor, configure the processor to:
   map branches of the blood vessel based on changes to the blood flow,
   generate an overlay image based on the shape sensing data, the overlay image indicating a shape of the blood vessel and locations of the branches,
   determine a count of a number of sealed branches, and
   cause the display to render the overlay image over a rendering of the blood vessel to provide a guide for visualizing the branches of the blood vessel, and update the overlay image to display the count of the number of sealed branches.

2. The system as recited in claim 1, wherein the instructions further configure the processor to use strain induced fluctuations measured by the fiber optic shape sensing device to determine a position of the blood vessel and the locations of the branches based upon the changes to the blood flow in the blood vessel.

3. The system as recited in claim 1, wherein the rendering includes an image of the blood vessel collected using an endoscope and the instructions further configure the processor to register the overlay image with the image of the blood vessel.

4. The system as recited in claim 3, further comprising a robot configured to guide one or more tools in accordance with the overlay image.

5. The system as recited in claim 4, wherein the one or more tools includes a tool to seal off the branches of the blood vessel to obtain the sealed branches.

6. The system as recited in claim 5, wherein the instructions further configure the processor to update the overlay image to indicate which branches have been sealed off.

7. The system as recited in claim 1, wherein the instructions further configure the processor to detect the branches based on a statistical analysis of the changes to the blood flow along a length of the blood vessel.

8. The system as recited in claim 1, wherein the instructions further configure the processor to include in the overlay image signposts at the locations of the branches to identify the locations of the branches.

9. The system as recited in claim 1, further comprising an imager configured to provide the rendering of the blood vessel as a real-time image.

10. The system as recited in claim 1, further comprising a tool configured to seal off the branches of the blood vessel to obtain the sealed branches.

11. A system for monitoring a blood vessel, comprising:
a processor;
a fiber optic shape sensing device configured to be inserted in a blood vessel for providing shape sensing data indicating blood flow in the blood vessel; and
a display,
wherein the processor is configured to:
map branches of the blood vessel based on changes to the blood flow,
generate an overlay image based on the shape sensing data, the overlay image indicating a shape of the blood vessel and locations of the branches,
determine a count of a number of sealed branches, and
cause the display to render the overlay image over a rendering of the blood vessel to provide a guide for visualizing the branches of the blood vessel, and display the count of the number of sealed branches.

12. The system of claim 11, further comprising a tool to seal off the branches of the blood vessel to obtain the sealed branches.

13. The system of claim 12, wherein the processor is further configured to update the number of the sealed branches when a further branch is sealed by the tool.

14. The system of claim 11, wherein the processor is further configured to update the overlay image to indicate which branches have been sealed off by a tool configured to seal off the branches of the blood vessel to obtain the sealed branches.

15. The system as recited in claim 11, wherein the processor is further configured to include signposts in the overlay image at the locations of the branches to identify the locations of the branches.

16. The system as recited in claim 11, further comprising an imager configured to provide the rendering of the blood vessel as a real-time image.

* * * * *